United States Patent
Scroggins

(10) Patent No.: US 7,335,806 B2
(45) Date of Patent: Feb. 26, 2008

(54) INTEGRATED PROCESS FOR PRODUCING 1,2-DICHLOROETHYLENE

(75) Inventor: Johnathan W. Scroggins, Lake Charles, LA (US)

(73) Assignee: PPG Industries Ohio, Inc., Cleveland, OH (US)

( * ) Notice: Subject to any disclaimer, the term of this patent is extended or adjusted under 35 U.S.C. 154(b) by 0 days.

(21) Appl. No.: 11/353,349

(22) Filed: Feb. 14, 2006

(65) Prior Publication Data

US 2007/0191653 A1    Aug. 16, 2007

(51) Int. Cl.
*C07C 19/00* (2006.01)
*C07C 17/00* (2006.01)

(52) U.S. Cl. ........................ 570/241; 570/243
(58) Field of Classification Search ........ 570/216, 570/219, 220, 222, 224, 243, 241
See application file for complete search history.

(56) References Cited

U.S. PATENT DOCUMENTS

| | | | |
|---|---|---|---|
| 2,951,103 A | 8/1960 | Ellsworth et al. | |
| 3,040,109 A | 6/1962 | Feathers et al. | |
| 3,256,352 A | 6/1966 | Bohl et al. | |
| 3,267,160 A | 8/1966 | McGreevy et al. | |
| 3,288,868 A | 11/1966 | Piester | |
| 3,449,450 A | 6/1969 | Bohl et al. | |
| 3,594,428 A | 7/1971 | Antonini et al. | |
| 3,642,918 A | * 2/1972 | Bohl | 570/224 |
| 4,816,609 A | * 3/1989 | Harley | 570/226 |
| 4,849,561 A | 7/1989 | Franklin | |
| 5,051,536 A | 9/1991 | Gorton et al. | |

FOREIGN PATENT DOCUMENTS

| | | |
|---|---|---|
| AT | 305 224 B | 2/1973 |
| GB | 1 265 245 | 3/1972 |
| GB | 1 267 169 | 3/1972 |
| GB | 1 335 998 | 10/1973 |

* cited by examiner

*Primary Examiner*—Karl Puttlitz
(74) *Attorney, Agent, or Firm*—Linda Pingitore

(57) ABSTRACT

Describes an integrated process for preparing 1,2-dichloroethylenes. In the described process organic feed material, e.g., $C_2$-$C_4$ aliphatic hydrocarbons and/or chlorinated derivatives of such aliphatic hydrocarbons, is introduced into a first reaction zone 10, e.g., a chlorination zone such as an oxychlorination zone, or a thermal cracking zone; first product effluent from the first reaction zone is forwarded to a second reaction zone 9; trichloroethane is introduced into the second reaction zone and into heat exchange contact with the first product effluent from the first reaction zone, which has a heat content sufficient to cause thermal dehydrochlorination of trichloroethane in the second reaction zone; and second product effluent is removed from the second reaction zone. 1,2-dichloroethylene is recovered by conventional distillation recovery methods from the second product effluent.

20 Claims, 1 Drawing Sheet

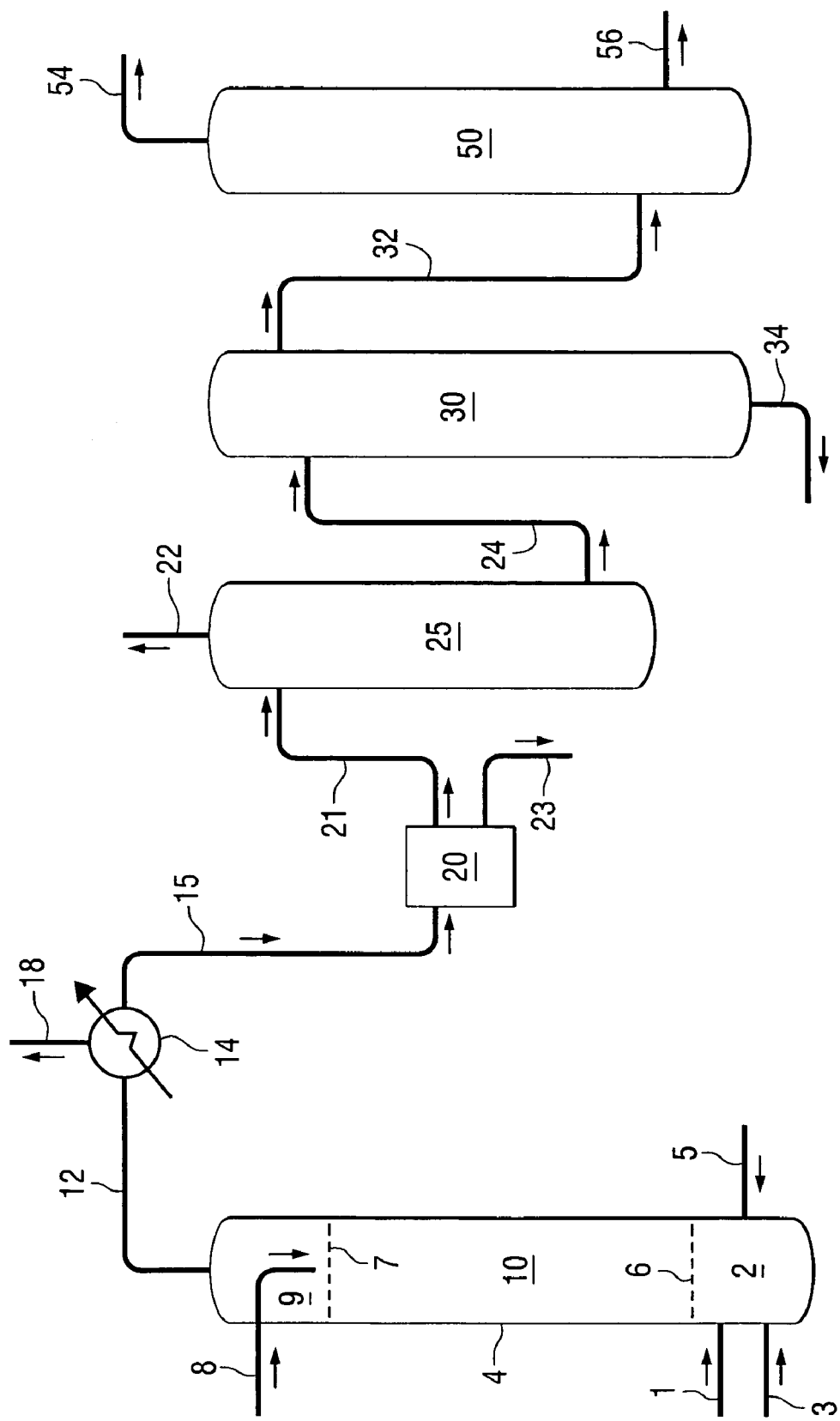

INTEGRATED PROCESS FOR PRODUCING 1,2-DICHLOROETHYLENE

FIELD OF THE INVENTION

The present invention relates to a process for producing 1,2-dichloroethylene. More particularly, the present invention relates to an integrated process for producing 1,2-dichloroethylene during the chlorination or thermal cracking of lower aliphatic hydrocarbons or their partially chlorinated derivatives. In particular, the present invention relates to an integrated process for producing 1,2-dichloroethylene as part of a process for producing trichloroethylene and perchloroethylene.

BACKGROUND OF THE INVENTION 1,2-dichloroethylene [CAS 540-59-0] is a material that has recently found increased utility for a variety of uses. 1,2-dichloroethylene can be named 1,2-dichloroethene and is also referred to as symmetrical dichloroethylene. 1,2-dichloroethylene exists as a mixture of two geometric isomers; namely, the trans isomer [CAS 156-60-5] and the cis isomer [CAS 156-59-2]. The isomers can be used separately or together in various proportions. It is reported that 1,2-dichloroethylene can be used as a low temperature extraction solvent for organic materials, such as dyes, perfumes, lacquers and thermoplastics, as a solvent for the manufacture of rubber solutions, as a coolant in refrigeration plants, and as a chemical intermediate in the synthesis of other chlorinated hydrocarbon solvents.

1,2-dichloroethylene can be produced by the direct chlorination of acetylene at temperatures of from approximately 40° C. to 80° C., or by the reduction of 1,1,2,2-tetrachloroethane. It is also formed as a by-product during the production of other $C_2$ chlorinated hydrocarbons, e.g., trichloroethylene. Recently, market requirements for 1,2-dichloroethylene have increased. Because of this increased demand, it would be desirable to find a means to produce increased amounts of 1,2-dichloroethylene without incurring the corresponding substantial capital investment required to build new manufacturing facilities for that purpose.

DESCRIPTION OF THE INVENTION

In accordance with the present invention, there is described an integrated process for preparing 1,2-dichloroethylene, which process comprises: (a) providing a first reaction zone chosen from a thermal cracking zone and chlorination zone, and a second reaction zone, (b) introducing organic feed comprising lower aliphatic hydrocarbons and/or chlorinated derivatives of such lower aliphatic hydrocarbons into the first reaction zone, (c) removing product effluent from the first reaction zone, the product effluent having a heat content that is at least sufficient to cause thermal dehydrochlorination of trichloroethane, (d) bringing trichloroethane into heat exchange contact with the product effluent from the first reaction zone in the second reaction zone, and (e) removing product effluent comprising 1,2-dichloroethylene from the second reaction zone.

BRIEF DESCRIPTION OF THE DRAWING

The sole FIGURE of this application is an abbreviated flow diagram of a contemplated embodiment of the present invention.

DETAILED DESCRIPTION OF THE INVENTION

For purposes of this specification (other than in the operating examples) or unless otherwise indicated, all numbers expressing quantities and ranges of ingredients, reaction conditions, etc that are used in the following description and claims are to be understood as modified in all instances by the term "about". Accordingly, unless indicated to the contrary, numerical parameters set forth in this specification and attached claims are approximations that may vary depending upon the results to be obtained by the process of the present invention. At the very least, and not as an attempt to limit the application of the doctrine of equivalents to the scope of the attached claims, each numerical parameter should at least be construed in light of the number of reported significant digits and by applying ordinary rounding techniques. Further, as used in this specification and the appended claims, the singular forms "a", "an", "said" and "the" are intended to include plural referents, unless expressly and unequivocally limited to one referent.

Notwithstanding that the numerical ranges and parameters setting forth the broad scope of the invention are approximations, numerical values set forth in specific examples are reported as precisely as possible. Any numerical value, however, inherently contains certain errors necessarily resulting from the standard deviation found in their respective testing measurements. Also, it should be understood that any numerical range recited herein is intended to include all sub-ranges subsumed therein. For example, a range "1 to 10" is intended to include all sub-ranges between and including the recited minimum value of 1 and the recited maximum value of 10; namely, a range having a minimum value equal to or greater than 1 and a maximum value of equal to or less than 10. Because the disclosed ranges are continuous, they include every value between the minimum and maximum values. Unless expressly indicated otherwise, the various numerical ranges specified in this application are, as stated, approximations.

As used in the following description and claims, the following terms have the indicated meanings:

The term "lower aliphatic hydrocarbon" means a saturated or ethylenically unsaturated hydrocarbon containing from 2 to 4 carbon atoms, or mixtures of such saturated and ethylenically unsaturated lower aliphatic hydrocarbons. Non-limiting examples of lower aliphatic hydrocarbons include ethane, ethylene, propane, propylene, the butanes and the butylenes.

The term "chlorinated derivative of lower aliphatic hydrocarbon" means a lower aliphatic hydrocarbon wherein at least one of the hydrogen atoms of the lower aliphatic hydrocarbon has been replaced with chlorine. Non-limiting examples of such chlorinated derivatives include ethyl chloride, tetrachloroethane, perchloroethylene and the chlorinated derivatives described in connection with the term "partially chlorinated derivative of lower aliphatic hydrocarbon." The term "chlorinated derivative of lower aliphatic hydrocarbon" includes the term "partially chlorinated derivative of lower aliphatic hydrocarbon".

The term "partially chlorinated derivative of lower aliphatic hydrocarbon" means a lower aliphatic hydrocarbon wherein at least one but not all of the hydrogen atoms associated with the carbon atoms of the lower aliphatic hydrocarbon is replaced by chlorine. Non-limiting examples of a partially chlorinated lower aliphatic hydrocarbon include dichloroethane, dichloroethylene, trichloroethane, trichloroethylene, vinyl chloride, vinylidene chloride, etc.

The term "1,2-dichloroethylene" or "DCE" includes trans 1,2-dichloroethylene, cis 1,2-dichloroethylene and mixtures of trans and cis-1,2-dichloroethylene.

The term "trichloroethane" or "TCE" includes 1,1,1-trichloroethane, 1,1,2-trichloroethane or mixtures of 1,1,1- and 1,1,2-trichloroethane.

The term "catalyst bed" means a bed of particulate catalyst materials, e.g., particulate oxychlorination catalytic materials, and includes a fixed or static catalyst bed, a dynamic catalyst bed, and a fluidized bed wherein the particles in the fluidized bed assume a highly turbulent condition that resembles a boiling liquid.

The term "oxychlorination" means a process wherein hydrogen chloride and/or chlorine is utilized as a chlorinating agent for the catalytic chlorination of a lower aliphatic hydrocarbon and/or a partially chlorinated derivative of a lower aliphatic hydrocarbon in the presence of oxygen. In one non-limiting embodiment, the process involves the reaction of gaseous hydrogen chloride, an oxygen-containing gas and an organic feed material comprising lower aliphatic hydrocarbon and/or partially chlorinated derivative of a lower aliphatic hydrocarbon in the presence of a particulate oxychlorination catalyst. It is postulated that the oxychlorination process involves oxidizing hydrogen chloride to free chlorine and water. The chlorine so produced reacts with the organic feed material to produce chlorinated hydrocarbon products. In a non-limiting modification of that oxychlorination process, chlorine is used as the feed gas in place of hydrogen chloride. In this modification, it is postulated that the chlorine reacts with the organic feed material to produce hydrogen chloride and chlorinated hydrocarbon products. The hydrogen chloride so produced is oxidized to chlorine and water, and such chlorine is used to achieve chlorination of the organic feed material.

The term "oxychlorination catalyst" means any of the known or later discovered catalytic materials that are used for oxychlorination or Deacon-type reactions. Non-limiting examples of such catalytic materials are metal halides, e.g., chlorides, impregnated on a suitable carrier or support. In alternate non-limiting embodiments, these metal halides can be chlorides of multivalent metals, such as copper, iron, chromium, zinc, and the like and mixtures of such multivalent metal halides. These multivalent metals may be utilized alone or combined with other metal chlorides, such as alkali metal chlorides, e.g., sodium and/or potassium chloride, alkaline earth metal chlorides, e.g., calcium chloride and/or magnesium chloride, or mixtures of such alkali metal chlorides and/or alkaline earth metal chlorides.

The oxychlorination catalyst is typically combined with a solid particulate carrier. Non-limiting examples of solid particulate carriers include silica, silica gels, alumina, alumina gels, calcium silicate, diatomaceous earth, Fuller's earth, kieselguhr, pumice and other like materials. The shape of the carrier particles can vary widely, e.g., the shape can be spherical, cylindrical or irregular, or the carrier particles can be a combination of such shaped particles. The selection of the particular solid carrier and shape depends, in part, upon the type of catalyst bed used, e.g., fixed bed or fluid bed, and the size and shape of the reactor used in the first reaction zone. In a non-limiting embodiment, the solid particulate carrier particles are between 10 and 400 mesh, as measured on Tyler standard screen scale sieves.

The term "oxygen-containing gas" means a gas that contains oxygen in amounts sufficient for use in the oxychlorination process and that is devoid of significant amounts of other gases that would have a deleterious effect on the oxychlorination process, such as a gas that will contaminate or deactivate the chlorination or oxychlorination catalyst, e.g., deleterious gases are substantially absent from the oxygen-containing gas. Non-limiting examples of an oxygen-containing gas include oxygen, e.g., elemental oxygen, air, oxygen-enriched air, etc.

The term "thermal cracking zone", as used in connection with the first reaction zone, means a reaction zone wherein heat induced dehydrochlorination of chlorinated and partially chlorinated derivatives of lower aliphatic hydrocarbon occurs (in the presence of or in the absence of a catalyst). A thermal cracking zone can also be referred to as a thermal pyrolysis zone.

The term "chlorination zone" or "thermal chlorination zone", as used in connection with the first reaction zone, means a reaction zone wherein chlorination of a lower aliphatic hydrocarbon and/or a partially chlorinated derivative of a lower aliphatic hydrocarbon occurs (in the presence of or in the absence of a catalyst).

In accordance with a non-limiting embodiment of the present invention, the first reaction zone is chosen from a chlorination zone or thermal cracking zone used for the chlorination and/or thermal cracking of a lower aliphatic hydrocarbon and/or chlorinated derivatives of a lower aliphatic hydrocarbon. In a particular non-limiting embodiment, the aliphatic hydrocarbon feed material charged to the first reaction zone comprises primarily saturated and unsaturated hydrocarbons having 2 carbon atoms and a chlorinated derivative of such hydrocarbons. The chlorination reaction can involve the use of chlorine or hydrogen chloride as the chlorinating agent; can utilize an oxygen-containing gas, as in the case of an oxychlorination reaction, and can be a catalytic or non-catalytic process. Non-limiting examples of reactions that can be used in the first reaction zone include the:

(a) thermal chlorination, e.g., oxychlorination, of 1,2-dichloroethane and/or trichloroethane to produce perchloroethylene and trichloroethylene, (b) thermal chlorination of 1,1-dichloroethane to produce methyl chloroform, (c) thermal oxychlorination of tetrachloroethane to produce perchloroethylene, (d) thermal chlorination of ethylene and/or ethane to produce chlorinated hydrocarbons having 2 carbon atoms, (e) thermal cracking of 1,2-dichloroethane to produce vinyl chloride, and (f) thermal cracking of trichloroethane to produce vinylidene chloride.

In accordance with alternate non-limiting embodiments of the present invention, the thermal chlorination/cracking reaction(s), which occurs in the first reaction zone, is performed under reaction conditions that either provides a first product effluent (from the first reaction zone) that has a heat content, e.g., a temperature, that is at least sufficient to cause catalytic or non-catalytic thermal dehydrochlorination of trichloroethane, or a first product effluent (from the first reaction zone) to which heat is added so that the first product effluent has the previously described heat content.

The first product effluent having the described heat content is forwarded to the second reaction zone. In the second reaction zone, trichloroethane is brought into heat exchange contact (direct or indirect) with the first product effluent, thereby to cause thermal dehydrochlorination of trichloroethane to TCE dehydrochlorinated products comprising 1,2-dichloroethylene. In a non-limiting embodiment, the first product effluent, e.g., gaseous product vapors emanating from the first reaction zone, is admixed directly with (commingled) with TCE in the second reaction zone, thereby to cause thermal dehydrochlorination of TCE in the second reaction zone. In an alternate non-limiting embodiment, the first product effluent is brought into indirect heat exchange with TCE in a second reaction zone, thereby to cause thermal dehydrochlorination of TCE. The second reaction zone may or may not contain a catalyst to increase the rate of dehydrochlorination of TCE.

The reactor comprising the first reaction zone can vary in type and design. The type of reactor used will depend on the particular reaction (thermal cracking or chlorination) performed in the first reaction zone and, if a catalyst bed, e.g., a fluid bed, is used, the type of catalyst bed. In one non-limiting embodiment, the first reaction zone comprises a catalyst bed housed in a tubular or elongated reactor having an internal diameter of from 2 inches to 24 inches (5 to 61 centimeters), e.g., 6 inches to 15 inches (15 to 38 centimeters). The length of the tubular reactor can vary and, in one non-limiting embodiment, can vary from 8 to 600 times the internal diameter of the tubular or elongated reactor. In a non-limiting embodiment, the length of the tubular or elongated reactor can be from 2 feet to 30 feet (0.6 to 9 meters), e.g., 8 feet to 15 feet (2.4 to 4.6 meters). In the case of a tubular reactor, it is common for a plurality of tubular reactors to be bundled together and housed within a reactor housing. A plenum chamber can be located in the reactor housing below the bundle of tubular reactors to allow for the introduction of reactant gases into the tubular reactors. A gas space or dome can be located above the tubular bundle within the reactor housing for collection of reaction product gases exiting the tubular reactor(s). A distributor plate can be positioned below the bundle of tubular reactors within the plenum chamber to allow for a uniform distribution of reactant gases into the tubular reactors. Similarly, a tube sheet can be used to hold the uppermost section of the tubular reactors in place within the space directly above the tubular reactors.

The reactor(s) comprising the first reaction zone is generally associated with a heat exchange system to withdraw the exothermic heat of reaction from the reactor(s). In a non-limiting embodiment, a bundle of tubular or elongated reactors comprising the first reaction zone is jacketed, and a heat exchange fluid circulates through the reactor jacket to control the temperature of the catalyst bed(s) within the tubular or elongated reactor(s). The reactor(s) comprising the first reaction zone is fabricated from materials of construction that are resistant to the thermal chlorination/cracking temperatures used, to the reactant feed materials, and to the products produced by the thermal chlorination/cracking reactions occurring within the reaction zone. Non-limiting examples of materials of construction for the reactor comprising the first reaction zone include mild steel, nickel, stainless steel, etc. A tubular reactor(s) comprising the first reaction zone can also be coated on its inner walls with a material resistant to the conditions existing within the reactor, e.g., temperature, pressure, organic/inorganic feed materials, products produced during the reaction, and corrosive materials such as chlorine, hydrogen chloride and hydrochloric acid that are charged to or produced within the reactor. A non-limiting example of such a coating material is a ceramic material.

The temperatures within the first reaction zone can vary and will depend in part on the particular reaction being performed in the first reaction zone, the organic feed to the reaction zone, the percent conversion desired for the organic feed, e.g., chlorinated lower aliphatic hydrocarbon, charged to the reaction zone, the desired selectivity of the products produced in the first reaction zone, the construction of the tubular reactor and the catalyst used. Generally, the temperature within the first reaction zone is at least 250° C. In alternate non-limiting embodiments, temperatures within the first reaction zone can vary from 250° C. to 700° C., such as from 340° C. to 500° C., e.g., from 375° C. to 450° C. The temperature within the first reaction zone can vary between any combination of the stated temperature values, including the recited temperatures.

Pressures within the first reaction zone can also vary, and will depend on the reactions being performed in the first reaction zone, the organic feed material, the catalyst, the temperatures used in the first reaction zone, etc. In a non-limiting embodiment, the pressure within the first reaction zone, e.g., within the tubular or elongated reactors, is maintained at or near atmospheric pressure for operational convenience; but, both pressures above and below atmospheric pressure can be used, if desired, provided that the reactions occurring in the first reaction zone can tolerate pressures other than atmospheric pressure, and the reactor is constructed to accommodate non-atmospheric pressures.

In accordance with the present invention, first product effluent from the first reaction zone, e.g., vaporous product effluent exiting from the top of tubular reactors comprising the first reaction zone, is removed from the first reaction zone and forwarded to a second reaction zone. This first product effluent has a heat content, e.g., enthalpy, that is at least sufficient to cause thermal dehydrochlorination of trichloroethane.

In accordance with the present invention, trichloroethane is brought into heat exchange contact with the first product effluent, e.g., the gaseous product effluent, produced in the first reaction zone, in the second reaction zone. In a non-limiting embodiment, trichloroethane is mixed directly (commingled) with the vaporous products produced in the first reaction zone; however, it is contemplated in another non-limiting embodiment that the trichloroethane is brought into indirect heat exchange with the products of the first reaction zone.

The second reaction zone may or may not contain a catalyst to increase the rate of dehydrochlorination of TCE. Use of a catalyst will depend upon the temperature of the effluent from the first reaction zone. Any known or later discovered catalyst used for the thermal dehydrochlorination of TCE can be used, e.g., catalysts known to those skilled in the art for the thermal cracking of TCE to vinylidene chloride.

Trichloroethane can be introduced into the second reaction zone as a liquid or gas. Preheating of the TCE prior to introducing it into the second reaction zone (in a non-limiting embodiment) to convert it from the liquid phase to the gas phase or merely to increase its temperature can be accomplished by a variety of methods, including but not limited to, passing it through a heat exchanger or by steam tracing the line feeding the TCE to the second reaction zone.

In a non-limiting embodiment, trichloroethane is introduced into the dome or gas space within the reactor housing above the tube sheet holding tubular or elongated reactors comprising the first reaction zone where it mixes directly with the first product effluent exiting from the top of the tubular or elongated reactors. In this embodiment, the dome or gas space in the reactor housing comprises the second reaction zone. The location where TCE is introduced into the gas space can vary, provided that the location allows the TCE sufficient residence time within the gas space for it to dehydrochlorinate to products comprising 1,2-dichloroethylene. In alternate non-limiting embodiments, TCE can be introduced into the dome within the reactor housing at one location or at two or more locations.

The manner in which TCE is injected into the second reaction zone can vary. In a non-limiting embodiment, the conduit(s) carrying TCE into the dome within the reactor housing holding a bundle of tubular reactors extends to a position just above, e.g., close to but spaced from, the top of the first reaction zone, e.g., just above the tube sheet containing the tubular reactors. In another non-limiting embodiment, the TCE is injected into the dome within the reactor housing in a manner such that the TCE blooms out into the second reaction zone to insure maximum mixing and heat transfer with the first product effluent from the first reaction zone. Such a mode of TCE injection avoids localized pockets of TCE or injection of the TCE as a jet that impinges on the top of the tube sheet holding the tubular reactors. In a further non-limiting embodiment, TCE and the first product effluent from the first reaction zone are mixed directly in a separate vessel comprising the second reaction zone.

As mentioned, TCE may be brought into indirect heat exchange with the product effluent from the first reaction zone. This can be accomplished by placing a conduit through which the TCE passes within the dome or gas space of the reactor housing comprising the first reaction zone, or placing such a conduit in a separate vessel outside the reactor housing comprising the first reaction zone. The conduit through which the TCE passes may contain a dehydrochlorination catalyst. Regardless of whether TCE is brought directly or indirectly into heat exchange contact with the product effluent from the first reaction zone, the temperature of the product effluent from the first reaction zone is at least sufficient to cause thermal dehydrochlorination (cracking) of the TCE.

The average temperature within the second reaction zone can vary. In a non-limiting embodiment, the temperature of the second reaction zone, e.g., the temperature to which the TCE is exposed, is at least 250° C., e.g., at least 340° C. In another non-limiting embodiment, the average temperature of the second reaction zone is less than 700° C., e.g., less than 500° C. In a further non-limiting embodiment, the average temperature of the second reaction zone varies from 340° C. to 500° C., e.g., from 375° C. to 450° C. The average temperature within the second reaction zone can range between any combination of the recited temperature values, including the specified values. The average temperature required will, of course, depend on whether the second reaction zone contains a catalyst to enhance the thermal dehydrochlorination of the TCE. If a catalyst is used, lower temperatures are required.

The temperature within the second reaction zone will depend of course on the temperature and volume of the vaporous first product effluent exiting from the first reaction zone, and the amount, temperature and physical state of the TCE introduced into the second reaction zone. If the TCE is introduced into the second reaction zone as a liquid, a portion of the heat content of the vaporous first product effluent will be used to vaporize the TCE. If the TCE is introduced into the second reaction zone as a gas, more of the heat content of the vaporous first product effluent is available for dehydrochlorinating (cracking) the TCE feed. Accordingly, the amount of TCE charged to the second reaction zone is regulated to take into account the amount of heat available from the first product effluent for thermal dehydrochlorination of the TCE and, if needed, for vaporizing any liquid TCE introduced into the second reaction zone.

A TCE dehydrochlorination (cracking) catalyst can be present within the second reaction zone. In particular, in a non-limiting embodiment, it is contemplated that when TCE is brought into indirect heat exchange with vaporous product effluent from the first reaction zone, e.g., when a separate reaction vessel is used as the second reaction zone, a catalyst may be present in such a separate reaction vessel.

The residence time that trichloroethane is in heat exchange contact with the product effluent from the first reaction zone (contact time) can vary, and will depend in part on the volume and feed rate of the organic feed charged to the first reaction zone and the volume of the second reaction zone. The residence time is sufficient to convert at least a portion of the trichloroethane to 1,2-dichloroethylene, e.g., by thermal dehydrochlorination. The percent trichloroethane that is dehydrochlorinated will be a function, in part, of the residence time. Generally, the longer the residence time at dehydrochlorination temperatures, the higher the amount of trichloroethane that is converted. In a non-limiting embodiment, the residence time is at least 3 seconds. While there is no upper limit for the contact time, economic considerations suggest that the contact time will be not more than 40 seconds. In alternate non-limiting embodiments, the residence time that TCE is in heat exchange contact with the product effluent from the first reaction zone can vary from 5 to 30 or 40 seconds, e.g., from 10 to 15 or 20 seconds. The residence time can vary between any combination of the stated lower and upper times, including the recited times.

The attached FIGURE is an abbreviated schematic of a process scheme for carrying out an embodiment of the present invention. In that FIGURE, the first reaction zone is represented as a multitubular reactor for converting an organic feed to perchloroethylene and trichloroethylene by a catalytic oxychlorination process. Although the integrated process of the present invention is exemplified in the attached FIGURE by an oxychlorination process for manufacturing perchloroethylene and trichloroethylene, one skilled in the art can readily adapt the concept of the invention described in this specification to other thermal chlorination/cracking processes for the production of other chlorinated and non-chlorinated lower aliphatic hydrocarbons, which processes have been described earlier in this description.

Referring now to the attached FIGURE, there is shown reactor 10, which comprises a housing 4 containing a bundle of elongated reactor tubes (not shown). The reactor tubes are jacketed to contain a heat exchange medium in order to maintain the temperature within the reactor tubes at the appropriate oxychlorination temperature, and reduce the number of hot spots that commonly occur within the reactor tubes. Each tube of the bundle contains an oxychlorination catalyst. The elongated reactor tubes comprise the first reaction zone.

Organic feed material is introduced into reactor 10 by means of line 1. The composition of the organic feed can vary, and will depend on the oxychlorination process being performed and the composition of recycle streams that may be recycled to reactor 10. In one non-limiting embodiment, the organic feed material comprises lower aliphatic hydrocarbon materials and their chlorinated derivatives. Non-limiting examples of compounds that can comprise the organic feed material include: trichloroethane, 1,2-dichloroethane, trichloroethylene, perchloroethylene, vinyl chloride, vinylidene chloride, 1,2-dichloroethylenes, tetrachloroethane, pentachloroethane and hexachloroethane The organic feed can be in a liquid or vaporous state. It can be preheated or vaporized by, for example, heat exchange with other process streams, or passing it through one or more heaters, e.g., steam heated reboilers.

Chlorinating agent, e.g., hydrogen chloride, is introduced into reactor 10 through line 3 and oxygen-containing gas is introduced into reactor 10 through line 5. The amount of oxygen-containing gas and chlorinating agent charged to reactor 10 will depend on the amount and composition of the organic feed, but should be sufficient, e.g., at least stoichiometric amounts, to oxychlorinate the amount of lower aliphatic hydrocarbons and their chlorinated derivatives that are to be converted by oxychlorination to trichloroethylene and perchloroethylene at the reaction conditions present within the reactor, e.g., temperature, pressure, catalyst, catalyst condition, flow rates, and the desired conversion rates and selectivity for the principal oxychlorination products.

The organic feed, chlorinating agent and oxygen-containing gas are introduced near the bottom of reactor 10 and below the tubular reactors, e.g., below distributor plate 6 (shown as a dotted line), such as into a plenum chamber or distribution zone 2, which is located below distributor plate 6. The oxychlorination reaction takes place within the reactor tubes of the multitubular reactor (first reaction zone), and reaction product gases (first reaction product effluent) flow from the top of the tubular reactors into gas space or dome 9 located within the top portion of reactor housing 10 above tube sheet 7 (shown as a dotted line) that forms the upper end of the tubular reactors.

The product effluent from the first reaction zone, e.g., reaction products from the oxychlorination reaction, comprises a mixture of chlorinated derivatives of the organic feed, e.g., the lower aliphatic hydrocarbons and their partially chlorinated derivatives present in the composition comprising the organic feed, as well as components of the organic feed that pass through the first reaction zone unchanged. Non-limiting examples of the principal chlorinated reaction products removed from the first reaction zone include, but are not limited to, perchloroethylene, trichloroethylene, trichloroethane, tetrachloroethane, pentachloroethane, 1,2-dichloroethylenes, hexachloroethane, vinyl chloride and vinylidene chloride. In addition, water, chlorine, hydrogen chloride, carbon dioxide and carbon monoxide are also found in the product effluent removed from the first reaction zone.

The temperature of the reaction product effluent from the first reaction zone that flows into the gas space or dome 9 of housing 10 has a heat content that is at least sufficient to cause thermal dehydrochlorination of trichloroethane, e.g., the first reaction product effluent has a temperature that can be described as a trichloroethane dehydrochlorination temperature. The temperature within the gas space or dome 9 of reactor 10 prior to the introduction of trichloroethane into that gas space is substantially the same as the temperature of the first reaction product effluent. In alternate non-limiting embodiments, the temperature of the first reaction product effluent can vary between 250° C. and 700° C., more particularly between 340° C. and 500° C.

In accordance with a non-limiting embodiment of the present invention, trichloroethane is introduced into the gas space or dome 9 of reactor 10 by means of line 8. In this embodiment, the gas space or dome 9 comprises the second reaction zone. As shown, the outlet of line 8 terminates above the top of tube sheet 7. In alternate non-limiting embodiments, the outlet of line 8 can terminate from 2 to 6 inches (5 to 15 centimeters), e.g., 4 inches (10 centimeters), above the top of tube sheet 7.

The amount of trichloroethane introduced into gas space 9 of reactor 10 can vary, and will depend, in part, on the heat content and volume of the reaction products entering the gas space from the top of the tubular reactors, the volume of gas space 9, and the temperature of the TCE introduced into the gas space. In a non-limiting embodiment, the amount of trichloroethane introduced into gas space 9 of reactor 10, based on the amount of organic feed charged to reactor 10, can range from a weight ratio of 0.001 to 4.0. In alternate non-limiting embodiments, the weight ratio of trichloroethane charged to gas space 9 of reactor 10, to the amount of organic feed charged to reactor 10 can range from 0.01 to 1, e.g., from 0.01 to 0.5, such as 0.07. The weight ratio of trichloroethane to organic feed can vary between any combination of the enumerated values, including the specified values. Further, such weight ratios also apply to the circumstance where a second reaction zone separate from the dome of reactor 10 is used.

Effluent removed from reactor 10 (second product effluent) comprising both the oxychlorination reaction products and products resulting from the thermal dehydrochlorination of trichloroethane is removed from reactor 10 by line 12, and forwarded to heat exchanger 14. Cooled product effluent from heat exchanger 14 is forwarded to phase separation vessel 20 by line 15. A small portion of the product effluent from heat exchanger 14, e.g., from 2 to 15 weight percent, comprising uncondensed gases is sent to gas scrubbing equipment, such as a gas absorber, by line 18 and thereafter treated to remove hazardous components, e.g., incineration, prior to emission to the atmosphere.

In phase separation vessel 20, the crude organic phase of the cooled product effluent is separated from a liquid acid (hydrochloric acid) phase. The liquid acid phase is removed from separation vessel 20 by means of line 23. The crude organic phase is forwarded to drying column 25 by means of line 21, wherein water, hydrogen chloride and other uncondensed gases are separated from the crude organic product. These lower boiling materials are removed from drying column 25 through line 22.

The dried crude organic product is forwarded by line 24 to distillation column 30 wherein trichloroethylene and other lower boiling products are separated from perchloroethylene and other higher boiling products. The trichloroethylene-containing product stream is forwarded to distillation column 50 by line 32, while the perchloroethylene-containing stream is forwarded to a second distillation zone (not shown) by means of line 34.

The trichloroethylene-containing product stream forwarded to distillation column 50 is separated into its major components. The trichloroethylene product stream is removed from column 50 through line 56. This product can be neutralized, dried and forwarded to product storage where stabilizers can be added to it to prevent its decomposition. A stream comprising 1,2-dichloroethylenes and other chlorinated hydrocarbons boiling at a temperature less than trichloroethylene is removed from column 50 by means of line 54 and forwarded to a distillation zone (not shown) where cis 1,2-dichloroethylene and trans 1,2-trichloroethylene are, if required, separated.

Introducing trichloroethane (TCE) into the gas space 9 at the top of oxychlorination reactor 10, allows the preparation of greater amounts of 1,2-dichloroethylene material than would be produced as a by-product in the oxychlorination reaction. All of the 1,2-dichloroethylene product is eventually recovered from stream 54 that is removed from column 50. The described integrated process thereby permits the production of more of a desired product, e.g., 1,2-dichloroethylenes, without the need for additional significant capital investment in equipment.

The invention is further described in conjunction with the following examples, which are to be considered as illustrative rather than limiting, and in which all parts are by weight and all percentages are weight percentages unless otherwise specified.

In the following examples, a multitubular commercial size oxychlorination reactor was used. This reactor was used for the preparation of perchloroethylene and trichloroethylene. The reactor comprised a circular housing that contained multiple tubes filled with an oxychlorination particulate catalyst comprising metallic halide compounds. The reactor tubes were arranged within the housing in a triangular pitch and were held in place by a circular horizontal tube sheet at the top terminus of the tubes and a circular distributor plate at the lower terminus of the tubes. The reactor tubes were jacketed with a heat exchange medium to control the temperature within the tubes. The reactor was equipped with a conventional steam heated reboiler for heating the organic feed material, a heat exchanger for condensing the crude product removed from the top of the reactor housing, and other appropriate pumps, etc for carrying out the oxychlorination reaction.

EXAMPLE 1

An organic feed material comprising principally approximately 26 weight percent trichloroethane, 29 weight percent perchloroethylene, 25 weight percent tetrachloroethanes and 5.2 weight percent pentachloroethane (with the balance of the feed being composed of smaller amounts of other saturated and unsaturated $C_2$ chlorinated compounds) was introduced into oxychlorination reactor 10 below distributor plate 6 in the reactor housing. The temperature of the organic feed material was approximately 270° F. (132° C.). Hydrogen chloride gas at a temperature of approximately 258° F. (125° C.), and oxygen-containing gas at a temperature of approximately 190° F. (87.7° C.) were introduced into the oxychlorination reactor below the distributor plate simultaneously with the organic feed material. The volume ratio of the organic feed to the hydrogen chloride reactant feed was approximately 3.2; while the volume ratio of the organic feed to the oxygen-containing gas reactant feed was approximately 1.7. The temperature in the gas space above the reactor tubes (the dome temperature) was approximately 742° F. (394° C.).

Analysis of samples of the liquid crude product removed from the phase separation vessel 20 showed that the product comprised approximately 60.4 weight percent perchloroethylene, approximately 26.9 weight percent trichloroethylene, and approximately 1.5 weight percent 1,2-dichloroethylenes. The remaining 11.2 weight percent of the crude product was composed of other chlorinated hydrocarbons, which included a mixture of primarily aliphatic $C_1$ and $C_2$ saturated and unsaturated compounds such as carbon tetrachloride, trichloroethane, symmetrical and unsymmetrical tetrachloroethane, and various unreported other chlorinated compounds.

A TCE feed stream comprising approximately 85 weight percent trichloroethane, 13 weight percent perchloroethylene and approximately 2 weight percent of various other chlorinated hydrocarbons, such as symmetrical and unsymmetrical tetrachloroethane and pentachloroethane, was introduced at a liquid feed rate of 0.75 gallons per minute (2.8 liters/min) into the dome of reactor 10 through a feed pipe having a slanted exit opening that terminated several inches above the tube sheet. The feed pipe was traced (250 psig, 1725 kPa, steam) to vaporize at least a portion of the TCE feed. The TCE feed was introduced into the southeast quadrant of the reactor in a manner such that the TCE feed impinged on the circular tube sheet rather than into the opening of a reactor tube.

The TCE feed was introduced into the dome of the reactor for a period of 6 hours. Over the period during which the TCE feed was introduced into the dome of the reactor, the temperatures within the four quadrants of the dome were lowered slightly due to the heat required to vaporize (if needed) and dehydrochlorinate the TCE feed. The temperatures in the southeast and southwest quadrants were lowered on the average of from 11 to 17 degrees Fahrenheit (6.8 to 10° C.), while the temperatures in the northeast and northwest quadrants were lowered on the average of from 5 to 7 degrees Fahrenheit (3.3 to 3.8° C.).

Three samples of crude liquid product were removed from phase separation vessel 20 at 2 hour intervals during the 6 hour TCE feed injection period. Analysis of these samples showed that the product comprised approximately 57.8 weight percent perchloroethylene, approximately 25.9 weight percent trichloroethylene, and approximately 2.25 weight percent 1,2-dichloroethylenes. The remaining approximately 14 weight percent of the crude product was composed of other chlorinated hydrocarbons, as described in connection with the earlier analysis of the crude product taken prior to injection of the liquid TCE feed.

The foregoing analyses shows that injection of the TCE feed into the dome of the reactor increased the production of 1,2-dichloroethylene compounds (2.25 weight percent versus 1.54 weight percent), which represents an approximate 46 percent increase.

EXAMPLE 2

The procedure of Example 1 was repeated except that the volume ratio of the organic feed to the hydrogen chloride reactant feed was approximately 2.1, and the volume ratio of the organic feed to the oxygen-containing reactant feed was approximately 1.3. The organic feed material comprised principally approximately 23.3 weight percent trichloroethane, 22.3 weight percent perchloroethylene, 22.5 weight percent tetrachloroethanes and 5.4 weight percent pentachloroethane (with the remaining 26.5 weight percent of the feed being composed of smaller amounts of other saturated and unsaturated $C_2$ chlorinated compounds). Further, the period during which the TCE feed was introduced into the dome of the reactor was approximately 15 hours. Samples were taken from the liquid reactor product in the phase separation vessel 20 at 2 hour intervals over the course of the test run. Analysis of the samples showed a 51.5 percent increase in the production of 1,2-dichloroethylenes above that produced prior to the introduction of the TCE feed to the dome of the reactor.

EXAMPLE 3

The procedure of Example 1 was repeated except that the volume ratio of the organic feed to the hydrogen chloride reactant feed was approximately 2.27, and the volume ratio of the organic feed to the oxygen-containing reactant feed was approximately 1.33. The organic feed material comprised principally approximately 30.7 weight percent trichloroethane, 13.45 weight percent perchloroethylene, 24.6 weight percent tetrachloroethanes and 5.5 weight percent pentachloroethane (with the remaining 25.5 weight percent of the feed being composed of smaller amounts of other saturated and unsaturated $C_2$ chlorinated compounds).

Further, the period during which TCE feed was introduced into the dome of the reactor was approximately 15 hours. Samples were taken from the liquid reactor product in the phase separation vessel 20 at 2 hour intervals over the course of the test run. Analysis of the samples showed a 85.5 percent increase in the production of 1,2-dichloroethylenes above that produced prior to the introduction of the TCE feed to the dome of the reactor.

Although the present invention has been described with reference to specific details of certain embodiments thereof, it is not intended that such details should be regarded as limitations upon the scope of the invention except insofar as they are included in the accompanying claims.

What is claimed is:

1. An integrated process for preparing 1,2-dichloroethylene comprising:
   (a) providing a first reaction zone chosen from a chlorination zone and a thermal cracking zone, and a second reaction zone,
   (b) introducing organic feed comprising lower aliphatic hydrocarbon, chlorinated derivative of lower aliphatic hydrocarbon, or mixtures of lower aliphatic hydrocarbon and chlorinated derivatives thereof into the first reaction zone,
   (c) removing first product effluent from the first reaction zone and introducing first product effluent into the second reaction zone, said first product effluent having a heat content sufficient to cause thermal dehydrochlorination of trichloroethane in the second reaction zone,
   (d) introducing trichloroethane into the second reaction zone and into heat exchange contact with first product effluent introduced into the second reaction zone, thereby to convert at least a portion of said trichloroethane to 1,2—dichloroethylene, and
   (e) removing second product effluent comprising 1,2-dichloroethylene from the second reaction zone.

2. The process of claim 1 wherein the organic feed to the first reaction zone comprises primarily aliphatic hydrocarbons containing 2 carbon atoms and chlorinated derivatives thereof.

3. The process of claim 2 wherein the first reaction zone is an oxychlorination reaction zone.

4. The process of claim 3 wherein product effluent from the oxychlorination reaction zone comprises chlorinated olefinic hydrocarbons chosen from trichloroethylene, perchloroethylene, and mixtures of trichloroethylene and perchloroethylene.

5. The process of claim 3 wherein the organic feed to the first reaction zone comprises 1,2-dichloroethane, and the first product effluent from the first reaction zone comprises perchloroethylene and trichloroethylene.

6. The process of claim 3 wherein the organic feed to the first reaction zone comprises trichloroethane, and the first product effluent from the first reaction zone comprises perchloroethylene and trichloroethylene.

7. The process of claim 2 wherein the average temperature within the second reaction zone is at least 250° C.

8. The process of claim 2 wherein the average temperature within the second reaction zone is less than 700° C.

9. The process of claim 7 wherein the average temperature within the second reaction zone ranges from 340° C. to 500° C.

10. The process of claim 7 wherein the average residence time within the second reaction zone of the trichloroethane introduced into the second reaction zone is at least 3 seconds.

11. The process of claim 10 wherein the average residence time within the second reaction zone of the trichloroethane introduced into the second reaction zone is less than 40 seconds.

12. The process of claim 10 wherein the average residence time within the second reaction zone of the trichloroethane introduced into the second reaction zone ranges from 5 to 40 seconds.

13. The process of claim 2 wherein the weight ratio of the trichloroethane introduced into the second reaction zone to the organic feed introduced into the first reaction zone is from 0.001 to 4.0.

14. The process of claim 1 wherein first product effluent removed from the first reaction zone in (c) is commingled with trichloroethane introduced into the second reaction zone.

15. An integrated process for preparing 1,2-dichloroethylene comprising
   (a) providing a first oxychlorination reaction zone and a second reaction zone,
   (b) introducing organic feed comprising primarily aliphatic hydrocarbons containing 2 carbon atoms and chlorinated derivatives thereof, oxygen-containing gas and chlorinating agent into said first reaction zone, thereby to produce a first product effluent comprising trichloroethylene and perchloroethylene,
   (c) removing vaporous first product effluent from the first reaction zone and forwarding first product effluent to said second reaction zone, said forwarded first product effluent having a heat content at least sufficient to cause thermal dehydrochlorination of trichloroethane in said second reaction zone,
   (d) introducing trichloroethane into the second reaction zone and into heat exchange contact with first product effluent forwarded from the first reaction zone, thereby to convert at least a portion of said trichloroethane to 1,2-dichloroethylene, and
   (e) removing second product effluent comprising trichloroethylene, perchloroethylene and thermal dehydrochlorination products of trichloroethane from the second reaction zone, wherein the thermal dehydrochlorination products of trichloroethane include 1,2-dichloroethylene.

16. The process of claim 15 wherein first product effluent removed from the first reaction zone in (c) is commingled with the trichloroethane introduced into the second reaction zone.

17. The process of claim 16 wherein the commingled first product effluent and trichloroethane are in a vaporous state within the second reaction zone.

18. The process of claim 17 wherein the average temperature within the second reaction zone ranges from 340° C. to 500° C., and the average residence time of trichloroethane introduced into the second reaction zone in (d) is at least 3 seconds.

19. The process of claim 18 wherein the weight ratio of the trichloroethane introduced into the second reaction zone to the organic feed introduced into the first reaction zone is from 0.01 to 1.0.

20. The process of claim 19 wherein the weight ratio of the trichloroethane introduced into the second reaction zone to the organic feed introduced into the first reaction zone is from 0.01 to 0.5.

* * * * *